United States Patent
Watabe et al.

(10) Patent No.: US 7,795,604 B2
(45) Date of Patent: Sep. 14, 2010

(54) DEVICE FOR MEASURING WEAR OF TROLLEY WIRE BY IMAGE PROCESSING

(75) Inventors: Yusuke Watabe, Numazu (JP); Makoto Niwakawa, Numazu (JP)

(73) Assignee: Meidensha Corporation, Tokyo (JP)

( * ) Notice: Subject to any disclaimer, the term of this patent is extended or adjusted under 35 U.S.C. 154(b) by 13 days.

(21) Appl. No.: 12/293,244

(22) PCT Filed: Mar. 29, 2007

(86) PCT No.: PCT/JP2007/056822
§ 371 (c)(1),
(2), (4) Date: Sep. 16, 2008

(87) PCT Pub. No.: WO2007/114227
PCT Pub. Date: Oct. 11, 2007

(65) Prior Publication Data
US 2009/0079997 A1    Mar. 26, 2009

(30) Foreign Application Priority Data
Mar. 31, 2006    (JP) .............................. 2006-097239

(51) Int. Cl.
*G01B 11/04* (2006.01)
(52) U.S. Cl. ........................ 250/559.01; 250/559.04; 250/559.05; 250/559.07; 250/559.08
(58) Field of Classification Search ........ 250/559.11–559.48; 356/636
See application file for complete search history.

(56) References Cited

U.S. PATENT DOCUMENTS 5,848,181 A * 12/1998 Ogata ...................... 382/169

FOREIGN PATENT DOCUMENTS

| JP | 3-156303 A | | 7/1991 |
|---|---|---|---|
| JP | 3-160349 A | | 7/1991 |
| JP | 03156303 A | * | 7/1991 |
| JP | 5-014815 U | | 2/1993 |
| JP | 5-071921 A | | 3/1993 |
| JP | 8-304029 A | | 11/1996 |
| JP | 10-194015 A | | 7/1998 |
| JP | 2006-248411 A | | 9/2006 |

OTHER PUBLICATIONS

S. Kusumi, "Development of Electric-Train Overhead Wire Detecting and Measuring Device Using Road/Rail Vehicle," 114th Railway Technical Research Institute Monthly Report Summary, Sep. 22, 1998.

* cited by examiner

*Primary Examiner*—Georgia Y Epps
*Assistant Examiner*—Tony Ko
(74) *Attorney, Agent, or Firm*—Foley & Lardner LLP

(57) ABSTRACT

The present invention provides a trolley wire wear measurement device by image processing in which a line sensor is arranged vertically and upward on a roof of an inspection car so that the line sensor looks up to a trolley wire and a lighting means that illuminates the trolley wire is formed by arranging a plurality of point light sources in a straight line in a direction perpendicular to a travelling direction of the inspection car on the inspection car.

14 Claims, 4 Drawing Sheets

(a) REFLECTED LIGHT IS UNIFORM

BINARY OPERATION (b)

SEPARATION BETWEEN BACKGROUND AND WORN SURFACE IS EXECUTED VERY WELL (c) REFLECTED LIGHT IS NONUNIFORM

BINARY OPERATION (d)

PART OF WORN PORTION IS ASSIMILATED TO BACKGROUND

DEVICE FOR MEASURING WEAR OF TROLLEY WIRE BY IMAGE PROCESSING

TECHNICAL FIELD

The present invention relates to a device for measuring wear of a trolley wire by image processing. More specifically, the present invention concerns measurement of the wear of the trolley wire by image processing and, in particular, relates to a device for measuring a width of a worn portion of the trolley wire.

BACKGROUND OF THE INVENTION

On the trolley wire that supplies a power to a car of an electric railroad or railway, contact with a pantograph current collector occurs each time the car passes.

Because of this, the trolley wire is gradually worn out during an operation of the electric railway car, and if a replacement is not made, a rupture or breaking finally occurs and causes an accident.

A wear limit is then set for the trolley wire. By using the wear limit as an index of a change of the trolley wire, the trolley wire is changed and safety of the electric railway car is secured.

As a method of measuring the wear of the trolley wire, there are mainly two methods; one is a method that directly measures a thickness of the trolley wire, the other is a method that calculates a width of a trolley wire worn portion and transforms the wear width into the thickness of the trolley wire.

As the method measuring the width of the trolley wire worn portion, of the above methods, there is a method that measures the trolley wire worn portion by applying sodium lamp or laser light (refer to a Non-patent Document 1).

This is the one that uses the following relation; a lower portion of the trolley wire is a round gourd in shape, and, as the trolley wire is shaved by the wear and becomes flatter, the width of the shaved portion becomes wider. Then, the thickness of the shaved portion of the trolley wire is transformed from the wear width.

As the measuring method of the trolley wire worn portion, positions of a light source and a line sensor of a light receiving part are precisely adjusted so that a reflected light from the trolley wire worn portion is received with regular reflection when applying the sodium lamp or laser light from the light source, and the trolley wire worn portion is changed into a whiteout state by way of capturing and imaging an intense light by the regular reflection, then the width of the trolley wire worn portion is measured from a width of the whiteout portion which receives the intense light. This manner is a non-contact manner, thus a high speed operation is possible.

However, this manner is susceptible to noises such as a clamp that pinches the trolley wire and a structure which appears on the background. Further, in a case where a wrong measurement result is obtained due to some noises, there is no way to verify the result. Then, with regard to the portion of the problem as the wear of the trolley wire, it is verified using the method directly measuring the thickness of the trolley wire in the end. In addition, it is required that the regular reflection is received by precisely adjusting the positions of the light source and a light receiving device.

For these problems, in "TROLLEY WIRE ABRASION MEASURING DEVICE BY IMAGE PROCESSING (Patent Document 1)", there is no need to provide a special light for illumination, such as the sodium lamp and laser light, and a normal light can be used. Furthermore, the measurement can be carried out without requiring the precise adjustment of the position of the light source.

However, there is a problem in which unevenness of the reflected light that falls on or strikes the line sensor appears and it is difficult to create a uniform lighting condition.

Patent Document 1: Japanese Patent Application Kokai Publication No. 2006-248411

Non-patent Document 1: "Development of Electric-Train Overhead Wire Detecting and Measuring Device Using Road/Rail Vehicle", 114th Railway Technical Research Institute monthly report summary <Home page>http://www.rtri.or.jp/infoce/getsurei/1998/Getsu09/g114_5.html

SUMMARY OF THE INVENTION

As the measuring method of the wear or abrasion of the trolley wire, there are the following methods; the method in which the width of the trolley wire worn portion is measured by applying the sodium lamp or laser light and the thickness of the trolley wire is transformed or converted from the worn portion, and the trolley wire abrasion measuring method by image processing by applying the normal light like the Patent Document 1, and the following problems are raised.

(1) In the case of the method in which the width of the trolley wire worn portion is measured by applying the sodium lamp or laser light and the thickness of the trolley wire is transformed from the wear width, firstly, there is a need to prepare the special light for illumination, such as the sodium lamp and laser light. In particular, when using the laser light, because an influence on the human body must be taken into account, it requires careful handling. In addition, it is required that the regular reflection is received by precisely adjusting the positions of the light source and the light receiving device.

(2) In the case of the abrasion measuring method of the trolley wire by image processing like that disclosed in Patent Document 1, since a normal white lighting is used, the positioning adjustment etc. are easily achieved. However, because of the point light source, the light is the most intense or strongest at the center, and the light becomes weaker with distance from the center. For this reason, there is a problem in which the unevenness of the reflected light from the trolley wire appears, and it is difficult to create a uniform lighting condition.

A trolley wire wear measurement device by image processing, of the present invention, comprises: a line sensor picture image production means that produces a line sensor picture image by using a line sensor; a binary operation process means that gets a binary operated line sensor picture image by performing a binary operation for the line sensor picture image; a noise elimination process means that eliminates noises of the binary operated line sensor picture image; an edge detection process means that detects an edge of a trolley wire worn portion, as an edge data, from the noise eliminated binary operated line sensor picture image; and a trolley wire worn portion width calculation process means that calculates a width of the trolley wire worn portion on the basis of the edge data and a trolley wire height data, and wherein the line sensor is arranged vertically and upward on a roof of an inspection car so that the line sensor looks up to a trolley wire and a lighting means that illuminates the trolley wire is formed by arranging a plurality of point light sources in a straight line in a direction perpendicular to a travelling direction of the inspection car on the inspection car. With this device, the above problems are solved.

DETAILED DESCRIPTION

According to a trolley wire wear measurement device by image processing, of the present invention, the following effects are obtained.
(i) As compared with the method using a line light source, an intense lighting can be provided at low cost, and a uniform lighting condition having no unevenness of the reflected light can be created.
(ii) There is no need to use the special lighting.
(iii) As compared with the method using the laser light, there is no need to take account of the influence on the human body, and further handling is easy.
(iv) There is no inconvenience of precisely adjusting the positions of the light source and the light receiving device.
(v) The trolley wire wear measurement device can respond to an abrupt deviation or shift of the trolley wire, and can obtain the uniform reflected light.

(1) Basic Idea

An object of the present invention is to provide a measurement device for measuring the wear of the trolley wire by image processing.

Figure 1:
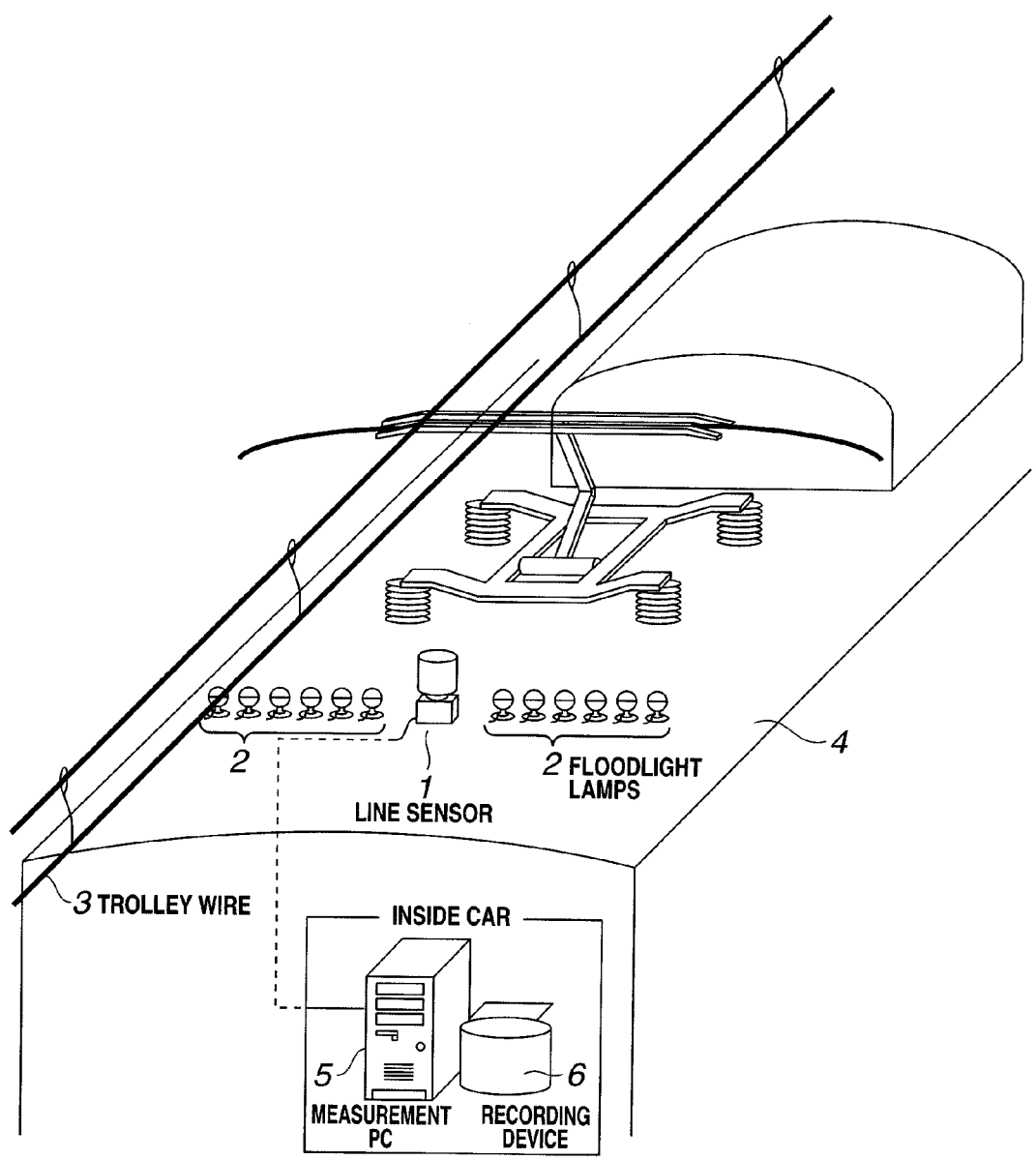
FIG. 1 is a perspective view that illustrates positions of a line sensor for measuring wear of a trolley wire and a lighting means.

As show in FIG. 1, the present invention uses, as an input means of picture image, for instance, a line sensor 1 that is arranged vertically and upward on a roof of an inspection car 4 so that the line sensor 1 looks up to a trolley wire 3.

The line sensor 1 is disposed so that its scanning line is perpendicular and horizontal to a direction of a travelling direction of the inspection car 4, and the scanning line crosses the trolley wire 3.

On the roof of the inspection car 4, as a lighting means, a plurality of small floodlight lamps or projectors 2, each of which is a point light source, are arranged on both left and right sides of the line sensor 1.

The floodlight lamps 2 are arranged in a straight line in a shift or deviation direction of the trolley wire on opposite sides of the line sensor 1. In order that the trolley wire 3 can be necessarily and adequately illuminated by the floodlight lamps 2, it is preferable that a width of the arrangement of the floodlight lamp 2 be substantially twice as large as a width of the deviation of the trolley wire.

Here, since a worn portion of the trolley wire 3 is a portion that is shaved by a pantograph, it has a high luster as compared with an unworn portion.

Therefore, by illuminating the trolley wire 3, a background portion and the other background portion can be separated at the worn portion of the trolley wire by the reflected light from a sliding or rubbing surface even on a line sensor picture image.

However, in the case of the point light source, if the unevenness is present in the reflected light from the worn portion, there is a possibility that the separation will not be able to be performed well upon a binary operation.

Figure 2A:
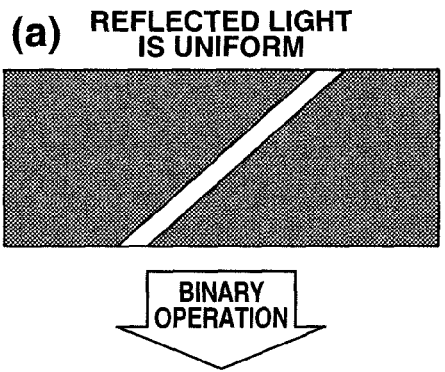
FIG. 2A is an explanation drawing that illustrates an example of a binary operation, of a case where a reflected light is uniform.
Figure 2A:
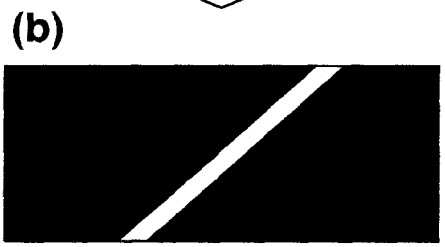
Figure 2B:
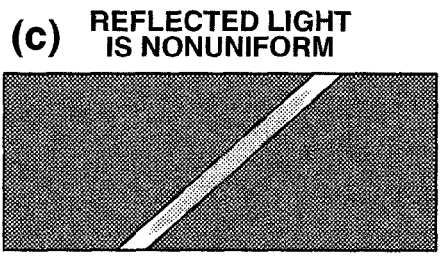
FIG. 2B is an explanation drawing that illustrates an example of the binary operation, of a case where the reflected light is nonuniform.
Figure 2B:
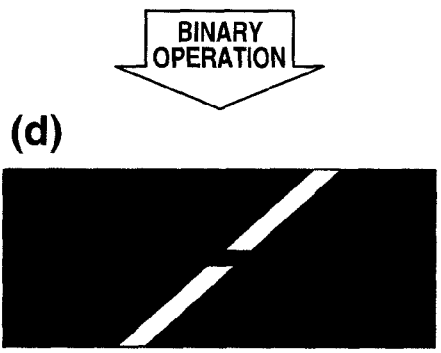

For example, as shown in FIG. 2B, if the reflected light is nonuniform, when performing the binary operation, a part of the worn portion of the trolley wire is assimilated to the background.

Further, in a case of a fluorescent light or lamp of the line light source, the light is too weak, thus the reflected light is not reflected on the line sensor.

Accordingly, in the present invention, by arranging the plurality of the point light sources in the straight line, the strong lighting which is regarded as the line light source can be provided at low cost. With this arrangement, it is possible to create the uniform lighting condition having no unevenness of the reflected light.

For instance, as shown in FIG. 2A, since the reflected light is uniform, when performing the binary operation, the separation between the background and a worn surface is executed very well.

A luminance or brightness signal of the scanning line, which is obtained by the line sensor 1, is output to a measurement personal computer (personal computer for processing) 5 that is installed inside the inspection car 4.

The measurement personal computer 5 arranges these luminance signals in time series and generates the line sensor picture image (plane or flat picture image) and it is stored in a recording device 6 as an input picture image.

The measurement personal computer 5 is the one that measures or determines the width of the trolley wire worn portion by image processing of the input line sensor picture image. With respect to a process from picture image acquisition and an output of a result, for instance, the same configuration as the Patent Document 1 could be used.

In the present invention, because of a non-contact manner, a high speed operation is possible, and a long distance section can be measured for a short period of time.

Further, the present invention does not require the special lighting, and does not have such difficulty of the handling that the laser light is used and the influence on the human body is taken into account. Moreover, unlike the case of the laser light or sodium lamp, there is no inconvenience of precisely adjusting the positions of the light source and the light receiving device.

In addition, even when the trolley wire heavily shifts upward and downward and to right and left, the uniform illumination can be applied.

(2) Addition of Half Mirror

In the case of the basic idea, as shown in FIG. 1, since the plurality of the floodlight lamps 2 of the lighting means are arranged on both left and right sides of the line sensor 1, there is a possibility that an area directly above the line sensor 1 will be low in brightness as compared with the other area.

Figure 3:
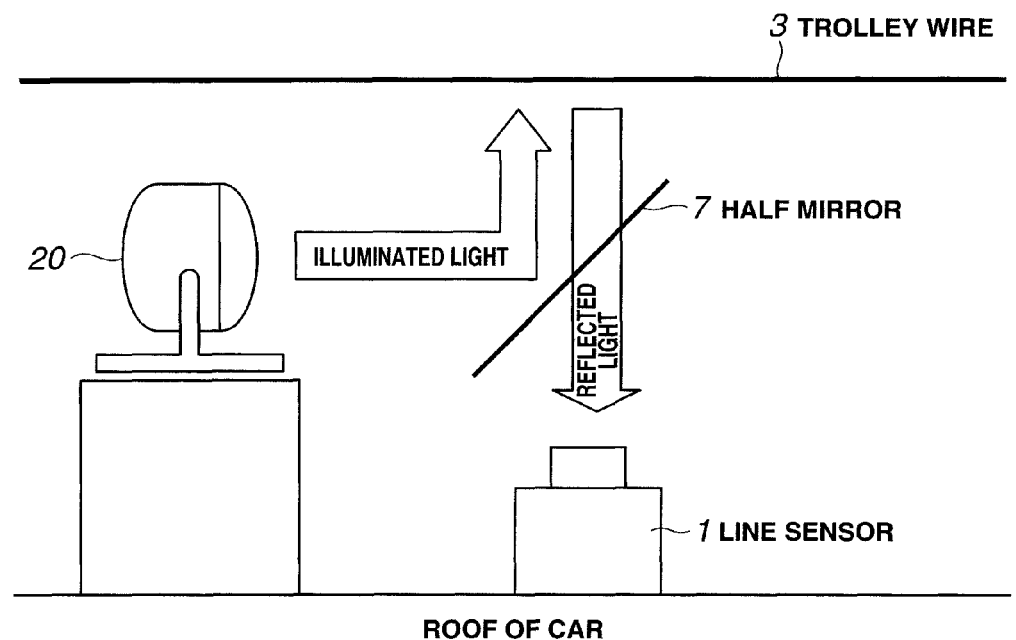
FIG. 3 is a side view that illustrates an example in which a half mirror is arranged between the line sensor and the trolley wire.

In order to solve the problem, as shown in FIG. 3, a half mirror 7 is arranged between the trolley wire 3 and the line sensor 1. The light applied from a lighting means 20 is reflected upward through the half mirror 7 and illuminates the trolley wire 3, while the picture image including the trolley wire 3 is, as the reflected light, captured by the line sensor 1 and imaged. The lighting means 20 is provided on a front or rear side of the line sensor 1. In FIG. 3, to simplify the drawing, the plurality of the floodlight lamps 2 arranged on both left and right sides of the line sensor 1 are omitted. The lighting means 20 could be the same type lighting as the floodlight lamps 2 in FIG. 1, or might be a different type lighting.

With this setting, since an adequate illumination is also applied to the area coaxially positioned with the line sensor 1, there is an advantage that the reflected light can be more uniform. Also in a case where the trolley wire shifts coaxially with a camera, since the reflected light can be directly obtained, an effect of creating a more uniform lighting condition can be produced.

Here, the trolley wire sways upward and downward and to right and left. For this reason, the object of the present invention is not achieved by an elevation angle fixed directional light. In the present invention, it is preferable that the light be applied in a direction parallel to an optical axis of the camera.

EMBODIMENT 1

Figure 5:
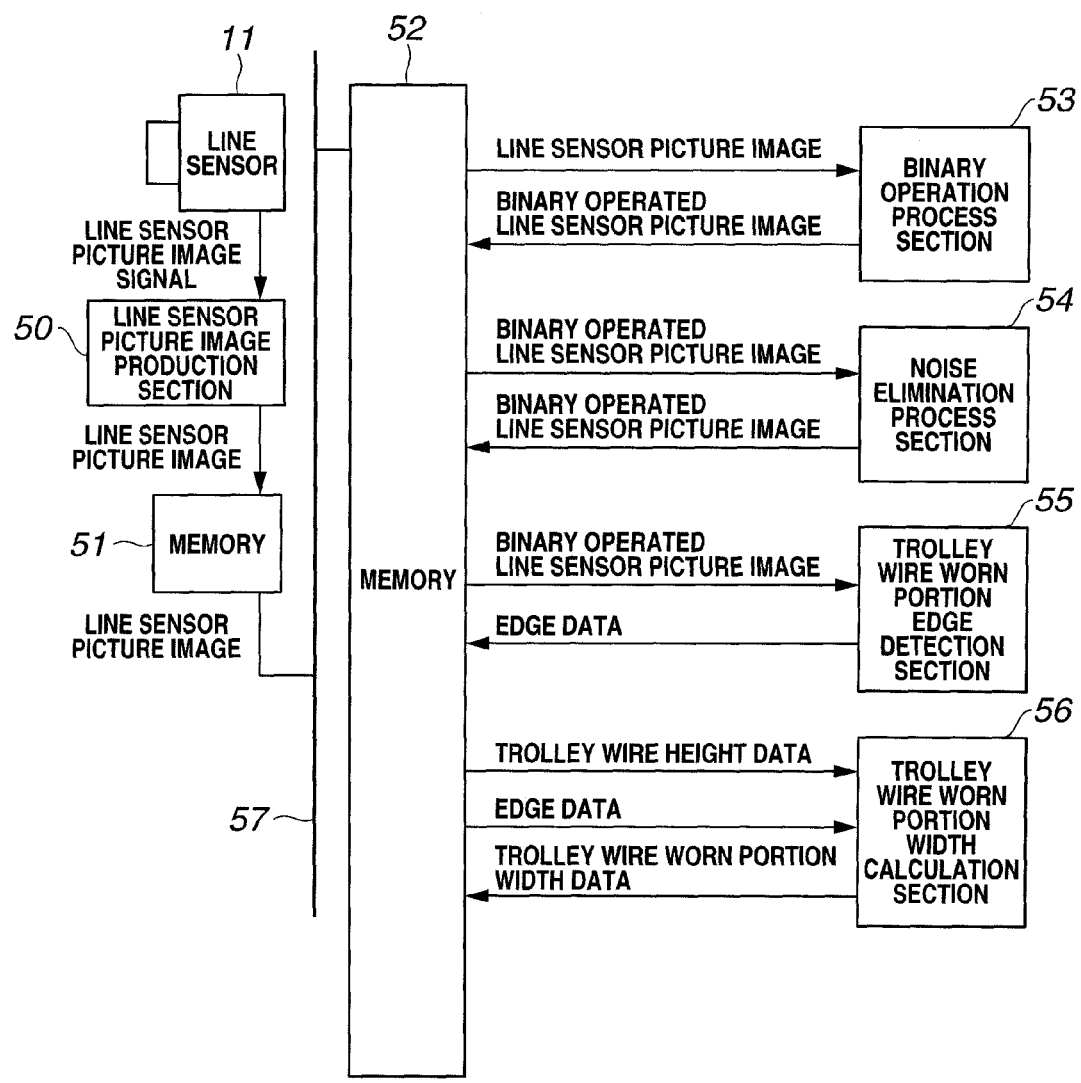
FIG. 5 is a block diagram of a trolley wire wear measurement device, according to a basic idea.

FIG. 5 illustrates the trolley wire wear measurement device by image processing of the embodiment 1 of the present invention. This embodiment concerns a specific configuration of the measurement personal computer 5 explained in the basic idea below.

Figure 4:
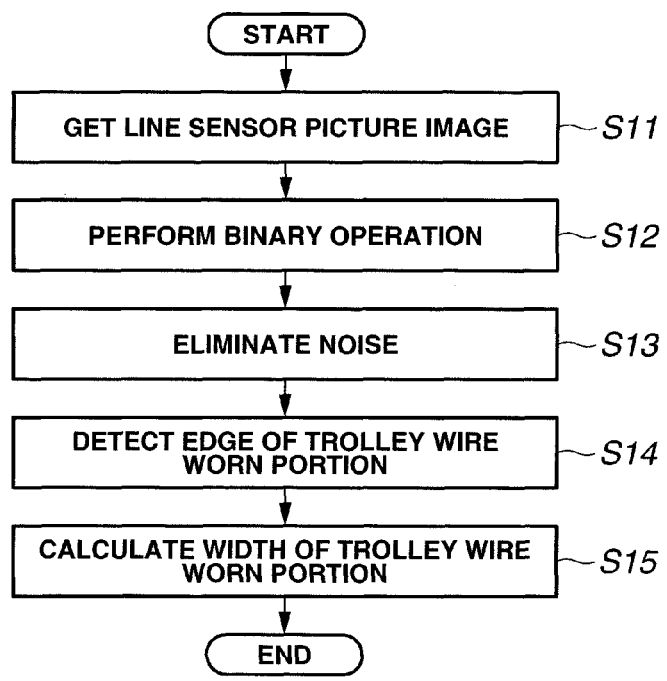
FIG. 4 is a flow chart for the measurement of the wear of the trolley wire, according to a basic idea.

That is, the measurement personal computer 5 has, as shown in FIG. 5, a line sensor picture image production section or means 50, a binary operation process section or means 53, a noise elimination process section or means 54, a trolley wire worn portion edge detection section or means 55, and a trolley wire worn portion width calculation section or means 56 and so on. The measurement personal computer 5 determines the width of the worn portion of the trolley wire by image processing of the line sensor picture image in accordance with a flow chart shown in FIG. 4.

First, the line sensor picture image production section 50 arranges the luminance signals of the scanning line obtained by the line sensor 11 in time series, and gets the line sensor picture image (step S11). A produced line sensor picture image is stored in the recording device 6 through a memory 51, and further is sent to the binary operation process section 53 through a memory 52.

Next, the binary operation process section 53 performs the binary operation for whole of the line sensor picture image, and gets a binary operated line sensor picture image (step S12).

The binary operated line sensor picture image is sent to the noise elimination process section 54 through the memory 52.

The noise elimination process section 54 eliminates fine spotted noises, which reside in the binary operated line sensor picture image due to a scratch of the trolley wire worn portion or a state of the background portion, by expansion, contraction processes of the binary operation (step S13).

The noise eliminated binary operated line sensor picture image is sent to the trolley wire worn portion edge detection section 55 through the memory 52.

In a case where a search is carried out from left hand side of a certain line, the trolley wire worn portion edge detection section 55 performs a detecting operation, in which a point that changes from black of the background to white of the worn portion is regarded as an edge point of a left side of the worn portion and a point that changes from white of the worn portion to black of the background is regarded as an edge point of a right side of the worn portion, from an upper part to a lower part of the picture image for each line, then detects the edge of the trolley wire worn portion of the binary operated line sensor picture image (step S14).

The detected both side edges of the trolley wire worn portion are sent, as an edge data, to the trolley wire worn portion width calculation section 56 through the memory 52 together with a trolley wire height data.

The trolley wire worn portion width calculation section 56 calculates a point-to-point distance of the both side edges on the one scanning line of the line sensor as the width on the picture image of the trolley wire worn portion by using the edge data of the both sides of the trolley wire worn portion, detected from the binary operated line sensor picture image, together with the height from the line sensor 1 to the trolley wire 3 (step S15).

The invention claimed is:

1. A trolley wire wear measurement device by image processing, comprising:
   a lighting means that illuminates a trolley wire;
   a line sensor that is arranged vertically and upward on a roof of an inspection car such that the line sensor looks up to the trolley wire, and receives a reflected light from a worn portion of the trolley wire;
   a line sensor picture image production means that produces a line sensor picture image on a basis of the reflected light received by the line sensor;
   a binary operation process means that gets a binary-operated line sensor picture image by performing a binary operation on the line sensor picture image;
   a noise elimination process means that eliminates noises of the binary-operated line sensor picture image;
   an edge detection process means that detects an edge of the worn portion of the trolley wire, as edge data, from the noise-eliminated binary-operated line sensor picture image;
   a trolley wire worn portion width calculation process means that calculates a width of the worn portion of the trolley wire on a basis of the edge data and height data of the trolley wire; and
   a half mirror that is arranged between the line sensor and the trolley wire,
   wherein a light applied from the lighting means is reflected upward through the half mirror and illuminates the trolley wire, while the picture image including the trolley wire is, from the reflected light, captured by the line sensor and imaged.

2. The trolley wire wear measurement device according to claim 1, wherein the lighting means has a plurality of point light sources on the inspection car and arranged in a straight line in a direction perpendicular to a traveling direction of the inspection car.

3. A trolley wire wear measurement device, comprising:
   a light projector configured to illuminate a trolley wire with projecting light;
   a line sensor configured to receive reflected light from the trolley wire;
   a half mirror configured to be arranged between the line sensor and the trolley wire; and
   an image processor configured to:
   produce a line sensor picture image based on the reflected light received by the line sensor,
   perform a binary operation on the line sensor picture image to produce a binary-operated line sensor picture image,
   detect edge data of a worn portion of the trolley wire based on the binary-operated line sensor picture image, and
   calculate a width of the worn portion of the trolley wire based on the edge data and height data of the trolley wire, wherein the half mirror is configured such that the projecting light from the light projector is reflected upward by the half mirror such that the trolley wire is illuminated and the reflected light from the trolley wire is received by the line sensor.

4. The trolley wire wear measurement device according to claim 3, wherein the light projector is one of a plurality of light projectors, and wherein the plurality of light projectors are configured to be arranged on a roof of an inspection car in a straight line in a direction perpendicular to a traveling direction of the inspection car.

5. The trolley wire wear measurement device according to claim 3, wherein the line sensor is configured to be arranged vertically and upward on a roof of an inspection car.

6. The trolley wire wear measurement device according to claim 3, wherein the image processor is further configured to first eliminate noise from the binary-operated line sensor picture image to produce a noise-eliminated binary-operated line sensor picture image, and then detect the edge data of the worn portion of the trolley wire from the noise-eliminated binary-operated line sensor picture image.

7. The trolley wire wear measurement device according to claim 6, wherein the image processor is configured to eliminate noise from the binary-operated line sensor picture image by eliminating fine spotted noises.

8. A trolley wire wear measurement device, comprising:
a light projector configured to illuminate a trolley wire with projecting light;
a line sensor configured to receive reflected light from the trolley wire;
a half mirror configured to be arranged between the line sensor and the trolley wire such that the projecting light is directed to the trolley wire and the reflected light is permitted to be received by the line sensor; and
an image processor configured to:
produce a line sensor picture image based on the reflected light received by the line sensor,
perform a binary operation on the line sensor picture image to produce a binary-operated line sensor picture image, and
determine a width of a worn portion of the trolley wire based on the binary-operated line sensor picture image.

9. The trolley wire wear measurement device according to claim 8, wherein the light projector is one of a plurality of light projectors, and wherein the plurality of light projectors are configured to be arranged on a roof of an inspection car in a straight line in a direction perpendicular to a traveling direction of the inspection car.

10. The trolley wire wear measurement device according to claim 8, wherein the line sensor is configured to be arranged vertically and upward on a roof of an inspection car.

11. The trolley wire wear measurement device according to claim 8, wherein the half mirror is configured such that the projecting light from the light projector is reflected upward by the half mirror such that the trolley wire is illuminated.

12. The trolley wire wear measurement device according to claim 8, wherein the image processor is configured to detect edge data of the worn portion of the trolley wire based on the binary-operated line sensor picture image.

13. The trolley wire wear measurement device according to claim 12, wherein the image processor is configured to calculate the width of the worn portion of the trolley wire based on the edge data and height data of the trolley wire.

14. The trolley wire wear measurement device according to claim 13, wherein the image processor is further configured to first eliminate noise from the binary-operated line sensor picture image to produce a noise-eliminated binary-operated line sensor picture image, and then detect the edge data of the worn portion of the trolley wire from the noise-eliminated binary-operated line sensor picture image.

* * * * *